US006132045A

United States Patent [19]
Gauvreau

[11] Patent Number: 6,132,045
[45] Date of Patent: Oct. 17, 2000

[54] EYEGLASS FRAME FITTING APPARATUS, KIT AND METHOD

[76] Inventor: Douglas K. Gauvreau, 12 Waites Landing Rd., Falmouth, Me. 04105

[21] Appl. No.: 08/947,697

[22] Filed: Oct. 9, 1997

Related U.S. Application Data

[60] Provisional application No. 60/028,447, Oct. 10, 1996.

[51] Int. Cl.$^7$ ........................................... A61B 3/10
[52] U.S. Cl. .................................... 351/204; 351/200
[58] Field of Search ............................. 351/204, 200, 351/41, 158

[56] References Cited

U.S. PATENT DOCUMENTS

| | | |
|---|---|---|
| 734,730 | 7/1903 | Millard . |
| 1,505,447 | 8/1924 | Uhlemann . |
| 2,197,139 | 4/1940 | Warner . |
| 2,326,030 | 8/1943 | Hearn . |
| 5,461,434 | 10/1995 | Blattberg . |

OTHER PUBLICATIONS

Pupilometer by Essilor Western Optical Ophthalmic Instrument Catalog, 1993–1994.
PD (pupil) distance millimeter ruler by Marchon Frames Surfacing & Finish Products (Date Unknown).

*Primary Examiner*—Hung Xuan Dang
*Attorney, Agent, or Firm*—Kirkpatrick & Lockhart

[57] ABSTRACT

An eyeglass frame fitting system is disclosed comprising a fitting frame with horizontal and vertical slides having apertures to measure horizontal pupil distance and vertical pupil position. Pupil location measurements are taken by viewing a distant target through the apertures which are aligned to allow unobstructed viewing of the target. The fitting frame also has temple slides to measure temple length. The fitting system also comprises a nose bar for measuring an individual's nose size and a head width slide for measuring an individual's head width. The fitting system is designed to be inexpensive and usable by any individual without the need for any technical knowledge or experience.

56 Claims, 10 Drawing Sheets

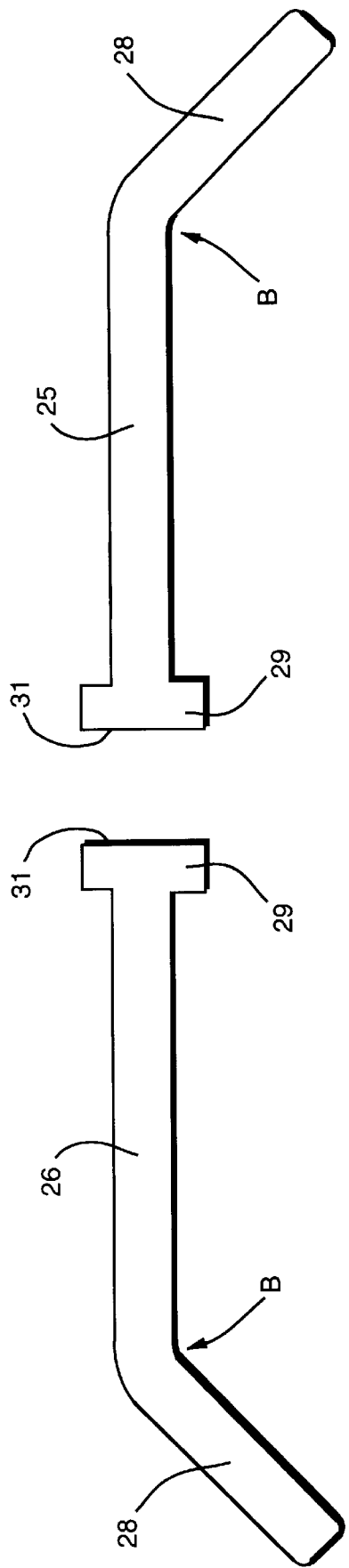
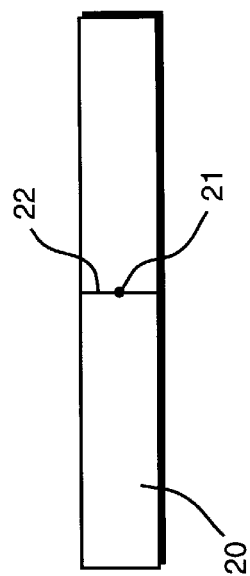
FIG. 8
FIG. 7
FIG. 6

EYEGLASS FRAME FITTING APPARATUS, KIT AND METHOD

CROSS-REFERENCE TO RELATED APPLICATIONS

The present application claims priority to Provisional Application Serial No. 60/028,447 filed Oct. 10, 1996, the teachings of which are incorporated herein by reference.

BACKGROUND OF THE INVENTION (1) Field of the Invention

This invention relates generally to apparatus for fitting eyeglass frames to an individual. More particularly, the present invention relates to an eyeglass frame fitting system that can be operated by any individual without the need for any special training or knowledge.

(2) Description of Related Art

In the typical case, when a person has diminished or impaired vision, such a person must have a highly-skilled optometrist or optician select corrective lenses along with eyeglass frames that are tailored to fit the particular individual's unique physical characteristics such as head shape and size. To accomplish this task, the optometrist or optician must either employ sophisticated mechanical devices, e.g., pupilometers (for example the Corneal Reflection Pupilometer by Essilor Technologies of America, Oldsmar, Fla.) and millimeter rulers (for example the PD (pupil distance) millimeter ruler by Marchon, Melville, N.Y.), that are used to take a variety of measurements needed to fashion eyeglass frames. Alternatively, the optometrist or optician must place an eyeglass frame of the exact size (eye size, bridge width and temple length) on the individual to determine fit.

Measurements that must be taken to fashion a properly fitting pair or eyeglass frames include horizontal pupil distance, vertical pupil height, nose width, temple length and head width. These measurements are taken to determine the optical center location of prescription eyeglass lenses that are incorporated into the eyeglass frames. In order to operate any of the known measuring devices properly, the device operator must first receive comprehensive training. Because sophisticated equipment and trained professionals have to be employed to take the necessary measurements, additional expense is unavoidably incurred.

Another problem associated with the use of sophisticated measuring devices, currently used in the field of optometry, which require skilled optometrists or opticians to operate the devices, concerns the potential for error in the measurements taken. The problem is inherent in the procedures used to take the measurements. For example, to take the horizontal and vertical pupil measurements, some of the older devices that are still in use require the trained operator to look through the device at the individual while making adjustments to the measuring device. With one such device, the operator aligns cross hairs in the measuring device with the individual's pupil. By following this procedure, the operator's eye is used to make the alignment. In doing so, the added element of the operator can lead to errors such as parallax. Any movement by the individual in relation to the measuring device, however slight and virtually imperceptible to the individual, when measurements are taken, could lead to measurement errors.

Similar problems arise with the use of millimeter rulers. For example, the PD (pupil distance) millimeter ruler (Marchon, Melville, N.Y.), requires an optician or trained technician to manipulate the ruler to take measurements. To operate the ruler, the optician or technician must align the ruler relative to the individual's head. Proper ruler alignment is crucial to obtain accurate measurements. Any error in ruler alignment by the optician or technician translates into inaccurate measurements and improper fitting eyeglass frames.

Following the measuring devices employing cross-hairs, the next generation of measuring devices, pupilometers, employ beams of light to take measurements of inter-pupil distance and to place the optical center in eyeglass frames. For example, a Corneal Reflection Pupilometer (Essilor Technologies of America, Oldsmar, Fla.) requires a technician to initially place the device on an individual's face over the individual's nose so that the individual looks through one side of the pupilometer. The centerline of the pupilometer must be aligned with the saggital plane of the individual's head in order to obtain accurate measurements.

The pupilometer contains lights which shine beams of light over the individual's pupils. The technician must manipulate the pupilometer to align the beams of light over the individual's pupils. When the light beams are centered over the pupils, readings are taken by the technician from calibrations on the pupilometer.

Due to the incorporation of light beam technology, pupilometers eliminate parallax problems. However, pupilometers are expensive and require the assistance of an optician or technician trained to use pupilometers.

Accordingly, there is a need for a cost effective eyeglass frame measuring device that can be operated by an individual in need of corrective lenses without any special training and without the measurement problems associated with the use of the sophisticated measuring devices currently in use.

SUMMARY OF THE INVENTION

It is, therefore, an object of the present invention to provide an eyeglass frame fitting system that can be operated by an untrained individual in need of eyeglasses. The system must provide the capability to take all the measurements necessary to make a proper fitting pair of eyeglasses.

Another object of the present invention is to provide a measurement system that eliminates the accuracy problems inherent with the use of sophisticated measuring devices and trained operators.

A further object of the present invention is to provide an eyeglass frame fitting system that is inexpensive and thus a cost effective way to obtain the measurements needed to fit eyeglass frames.

A still further object of the present invention is to use an aperture in the fitting system in conjunction with a reference point to enable an individual to accurately determine the optic center for each of the individual's eyes.

The eyeglass frame fitting system described herein includes a fitting frame with a plurality of adjustable sliding segments. The fitting frame has two temple slides that measure the length of the individual's temples. The temple slides have edge portions that abut calibrated temple scales affixed to either side of a body of the frame. The temple slides are slidably engaged to the body via vertical slots located in temple members adjacent to, and in mechanical connection to, a left and a right edge of the main body.

The fitting frame has two horizontal slides that measure the horizontal distance between the pupils. The horizontal slides have edge portions that abut calibrated horizontal scales affixed to the frame. The horizontal slides are slidably engaged to the body via vertical slots located in proximity to upper and lower edges of the body. The horizontal slides have lateral ends that extend beyond the vertical slots to enable the individual to grasp the lateral ends to adjust the slides in relation to the fitting frame body and the individual's pupil.

The fitting frame also has two vertical slides that measure the vertical position of the individual's pupils in relation to the head. The vertical slides have edge portions that abut calibrated vertical scales affixed to the horizontal slides. The vertical slides are slidably engaged to the horizontal slides via horizontal slots located in proximity to upper and lower edges of the horizontal slides. The ends of the vertical slides extend beyond the upper and the lower edges of the fitting frame body to allow the individual to move the vertical slides within the horizontal slots and thereby adjust the vertical slides. Apertures are situated at the center of each of the vertical slides.

The fitting system also comprises a head width slide that the individual uses to measure the overall width of the individual's head. The head width slide is comprised of two L-shaped segments that are in sliding engagement with each other. Each segment has a temple leg and a forehead leg. The temple legs are identical in width and length. One segment has a forehead leg with a calibrated scale affixed to a face of the forehead leg. The other segment has a forehead leg that has a width dimension greater than the width dimension of the forehead leg of the other segment. The larger forehead leg has head width slide slots. The forehead leg with the calibrated scale is in sliding engagement with the larger forehead leg via insertion into the head width slide slots. The larger forehead leg has an end which aligns with the calibrations of the scale. The L-shaped segments in combination can be adjusted to fit snugly around the individual's head.

The fitting system also comprises a nose bar. The nose bar has a series of incrementally sized parabolic-shaped curvatures extending inwardly along a longitudinal lower edge of the nose bar. The individual places the nose bar across the bridge of the individual's nose using the various openings until an opening is identified as fitting the most snug.

Finally, a method for determining the size of eyeglass frames is disclosed comprising: providing a fitting frame comprising a main body having temple members, horizontal slides, vertical slides with apertures and temple slides for measuring the horizontal pupil distance, vertical pupil position and temple length; placing the fitting frame on an individual's head to take horizontal pupil distance, vertical pupil position and temple length measurements; providing a head width slide for measuring an individual's head width; placing the head width slide on the individual's head to take a head width measurement; providing a nose bar having a plurality of incrementally-sized, parabolic-shaped curvatures on a bottom edge of the nose bar for measuring the individual's nose; and placing the nose bar on the bridge of the individual's nose to take a nose size measurement.

BRIEF DESCRIPTION OF THE DRAWINGS

FIG. 6 is a front view of a vertical slide according to one embodiment of the present invention.

FIG. 7 is an elevational view of a right temple slide according to one embodiment of the invention.

FIG. 8 is an elevational view of a left temple slide according to one embodiment of the invention.

DESCRIPTION OF THE PREFERRED EMBODIMENTS

The present invention generally relates to eyeglass frame fitting systems and in particular, eyeglass fitting frame systems that can be provided in kit form. The invention employs the novel feature of an aperture or pin hole to enable an individual in need of eyeglasses, to use his or her own eye to take precise measurements needed to fashion eyeglass frames to fit the particular individual's unique head geometry and pupil location and to ensure that the optical centers of prescription lenses placed in the eyeglass frames are properly oriented to the individual's eyes. By sighting a distant object through the apertures which are preferably small in diameter like pin holes and which are situated over the pupils, precise measurements can be taken. The apertures are aligned via manipulation of horizontal and vertical sliding members situated in a fitting frame. Calibrated scales are affixed on, or engraved into, the fitting frame adjacent to the sliding members so that measurements of the individual's horizontal pupil distance and vertical pupil position can be taken.

The individual's temple length is taken with temple slides also situated in the fitting frame. Additional measurements of the individual's nose width and head width are taken with a nose bar and head width slide respectively.

Figure 1:
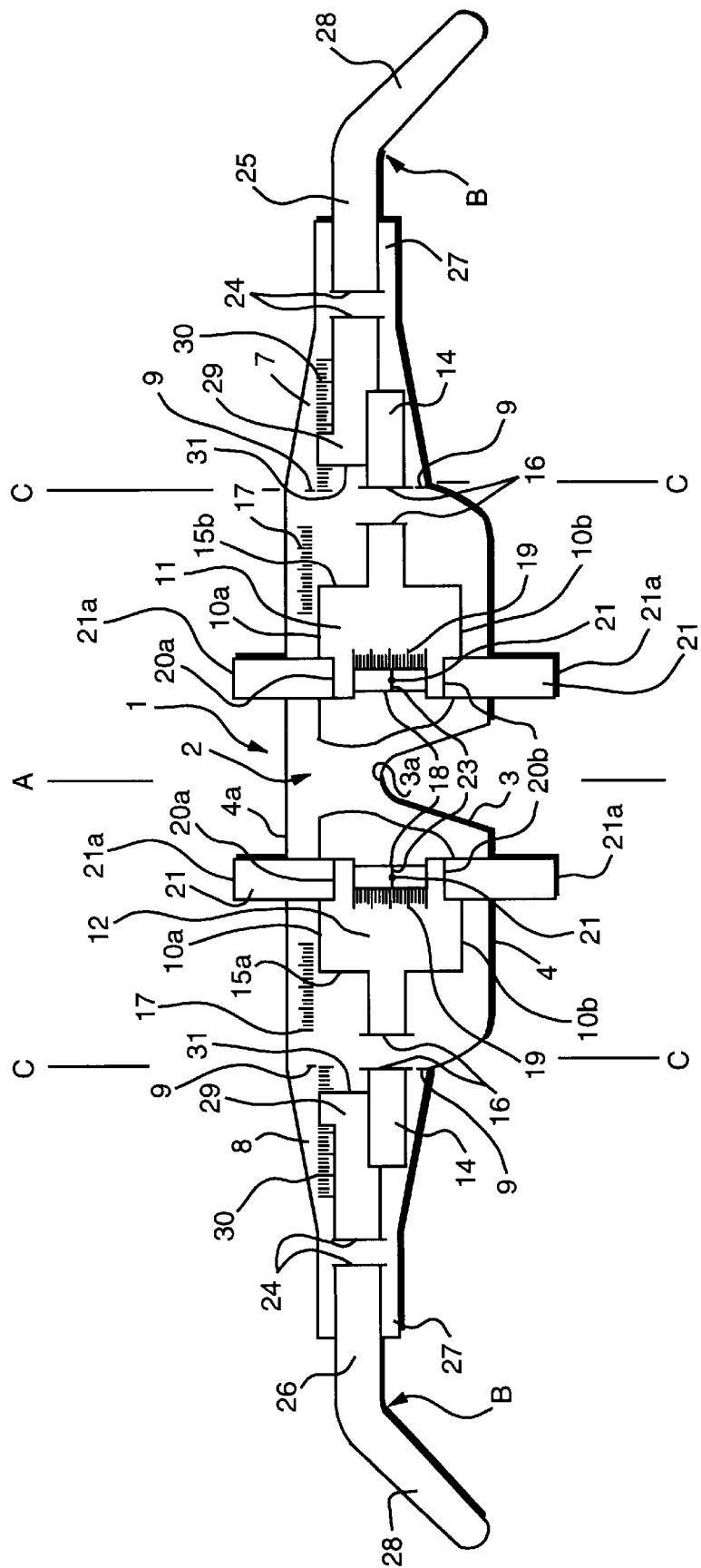
FIG. 1 is a front plan view of an assembled fitting frame according to one embodiment of the invention.
Figure 2:
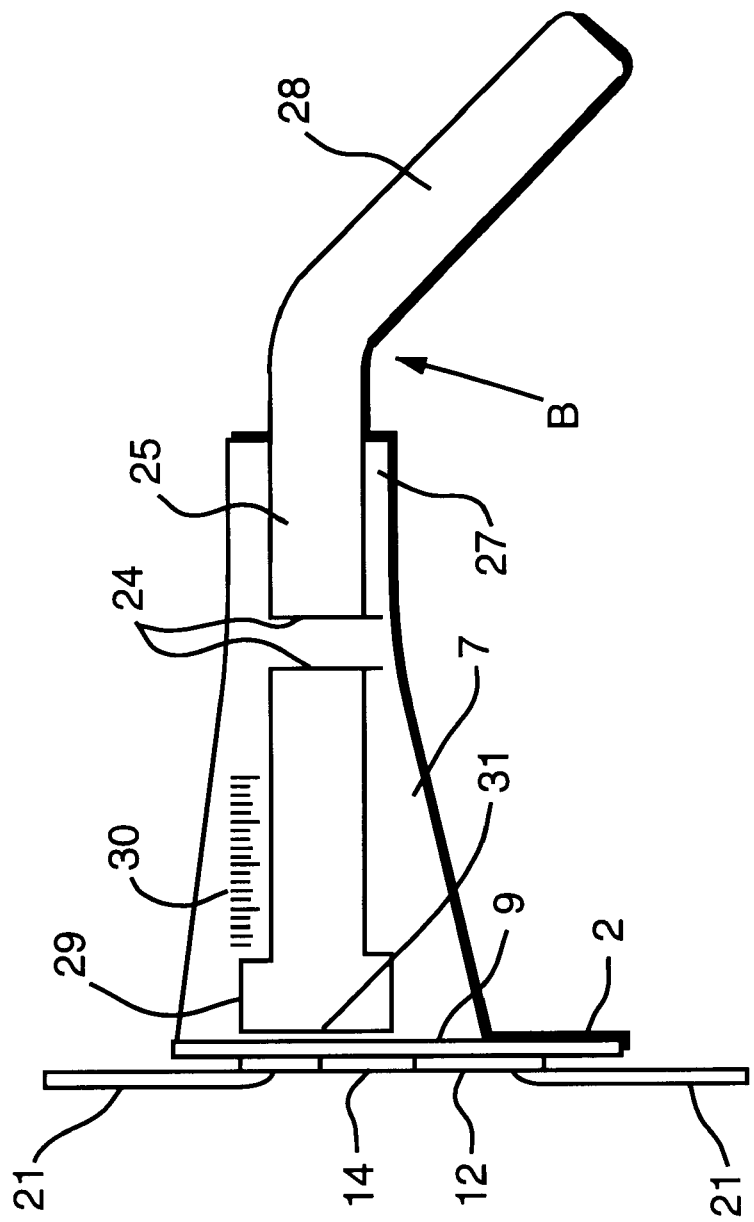
FIG. 2 is a side elevational view of an assembled fitting frame with a left ear member oriented approximately 90° from the plane of the main body and horizontal and vertical slides according to one embodiment of the invention.
Figure 3:
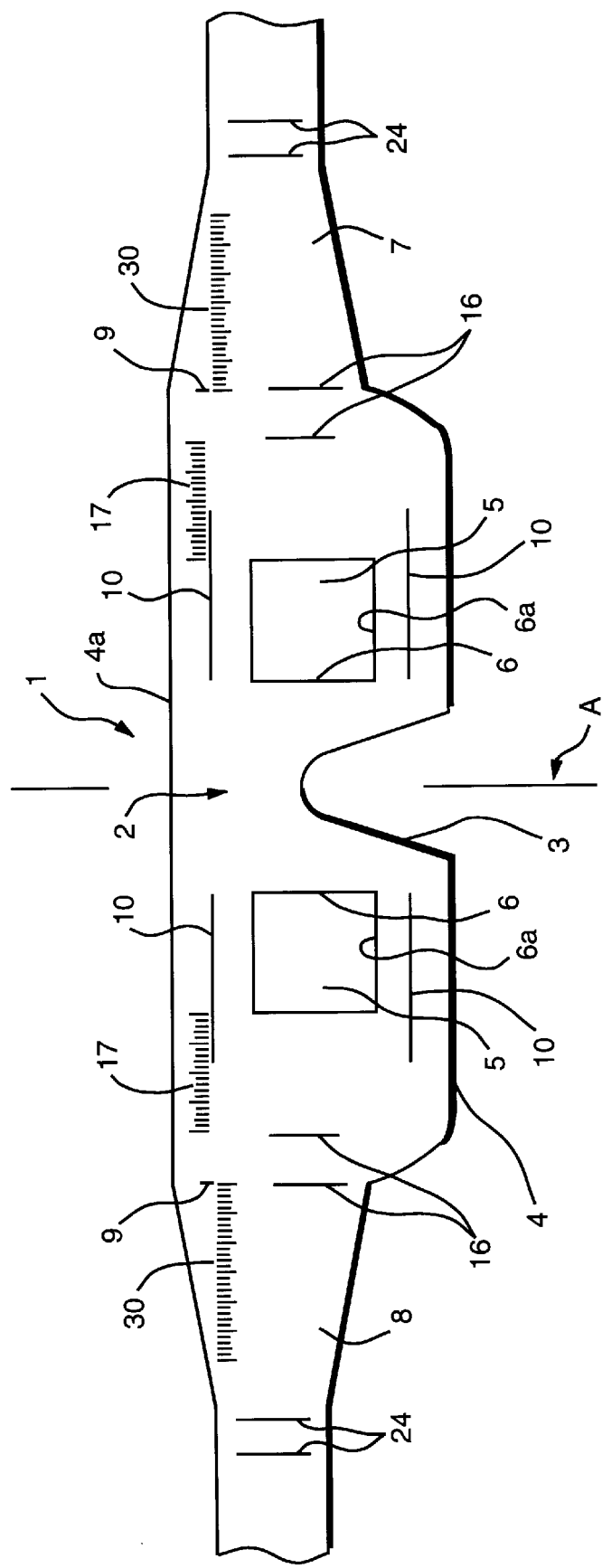
FIG. 3 is a front elevational view of a main body of a fitting frame with ear members oriented in the same plane of the main body according to one embodiment of the invention.

Referring to FIGS. 1, 2 and 3, it will be seen that the eyeglass frame fitting system of the present invention is comprised of a fitting frame 1 having a body 2. A parabolic-shaped curvature 3, adapted to matingly engage the contour of an individual's nose is situated about a centerline A of the body with ends terminating on a bottom edge 4 of the body. Preferably, curvature 3 has sides which are 8.5 millimeters (hereinafter "mm") from centerline A when taken from a point 10 mm below an apex 3a of curvature 3. Body 2 has portions defining two preferably square-shaped openings 5 which are situated equidistant from centerline A. Preferably, openings 5 are 22 mm in length and 22 mm in width dimensions. Ideally, openings 5 have opening inner edges 6 that are approximately 19 mm from centerline A and opening bottom edges 6a that are 14 mm from bottom edges 4 of body 2.

Situated on opposite sides of body 2 are a left temple member 7 and a right temple member 8. The temple members are in mechanical connection with body 2 and preferably are a continuous extension of body 2. The temple members are rotatable about an axis of connection C. If made of a material such as cardboard, vertical score lines 9 are engraved into the junction of body 2 and temple members 7 and 8 to ease folding of the temple members, i.e, rotation of the temple members about the score line in relation to the fitting frame body. Preferably, score lines 9 are situated 77 mm from centerline A. Temple members 7 and 8 are preferably 73 mm in length.

Situated above openings 5 are upper horizontal slide slots 10a and below openings 5 are lower horizontal slide slots 10b for receiving a left horizontal slide 11 and a right horizontal slide 12. Preferably, slots 10a and 10b are 30 mm in length, are situated 20 mm from centerline A with slots 10a situated 7 mm above openings 5 and slots 10b situated 7 mm below openings 5.

Figure 5:
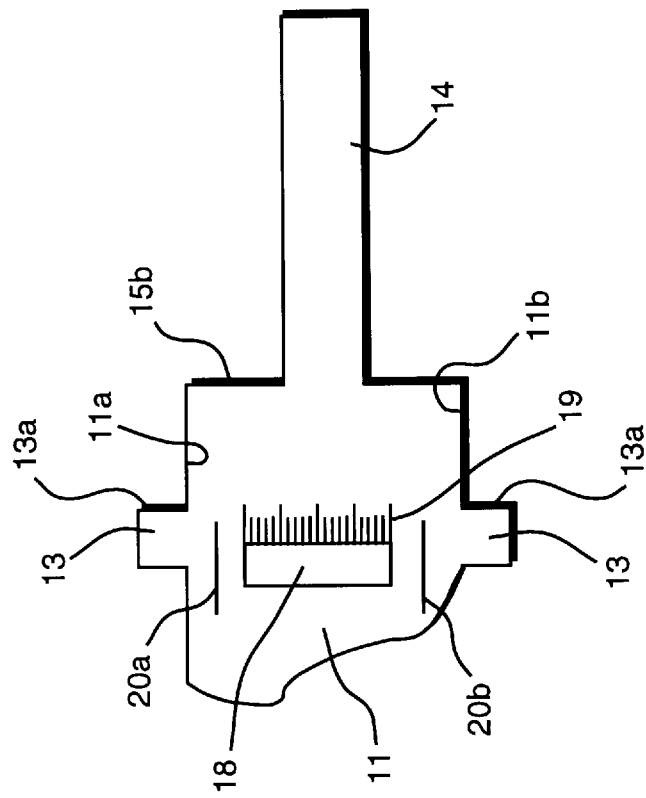
FIG. 5 is a front elevational view of a left horizontal slide according to one embodiment of the invention.
Figure 4:
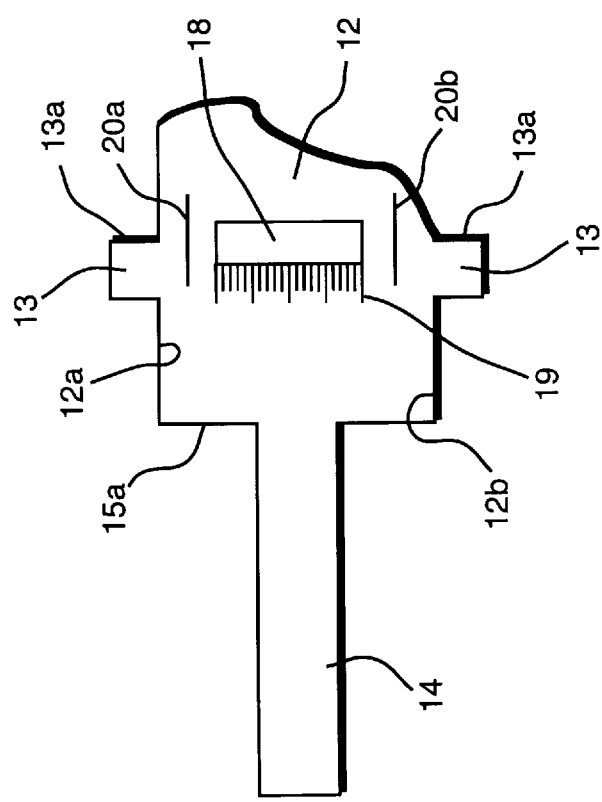
FIG. 4 is a front elevational view of a right horizontal slide according to one embodiment of the invention.

Referring to FIGS. 1, 4 and 5, horizontal slides 11 and 12 have tabs 13 adapted to slidingly engage body 2 via slots 10a and 10b. Elongated tabs 14 extend from lateral edge 15a of left horizontal slide 11 and from lateral edge 15b of right horizontal slide 12. Elongated tabs 14 are adapted to slidingly engage body 2 via paired elongated tab slots 16 in body 2. Preferably, paired elongated tab slots 16 are 12 mm in height with members of each pair being 8 mm apart with the innermost or medial slot 16 of each pair being 69 mm from centerline A. Preferably, vertical slots 16 are located 18 mm below an upper edge 4a of body 2.

Elongated tabs 14 extend beyond score lines 9 to allow an individual to grasp elongated tabs 14 to slide horizontal slides 11 and 12 along the length of horizontal slide slots 10a and 10b. Slides 11 and 12 are in mechanical, sliding engagement with body 2 via tabs 13 and elongated tabs 14.

Figure 13:
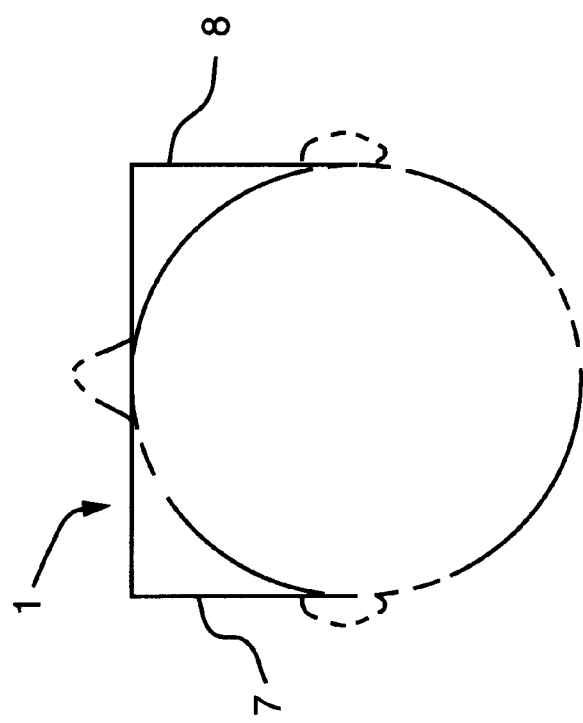
FIG. 13 is a top view of an assembled fitting frame, according to one embodiment of the present invention, placed around an individual's head.
Figure 15:
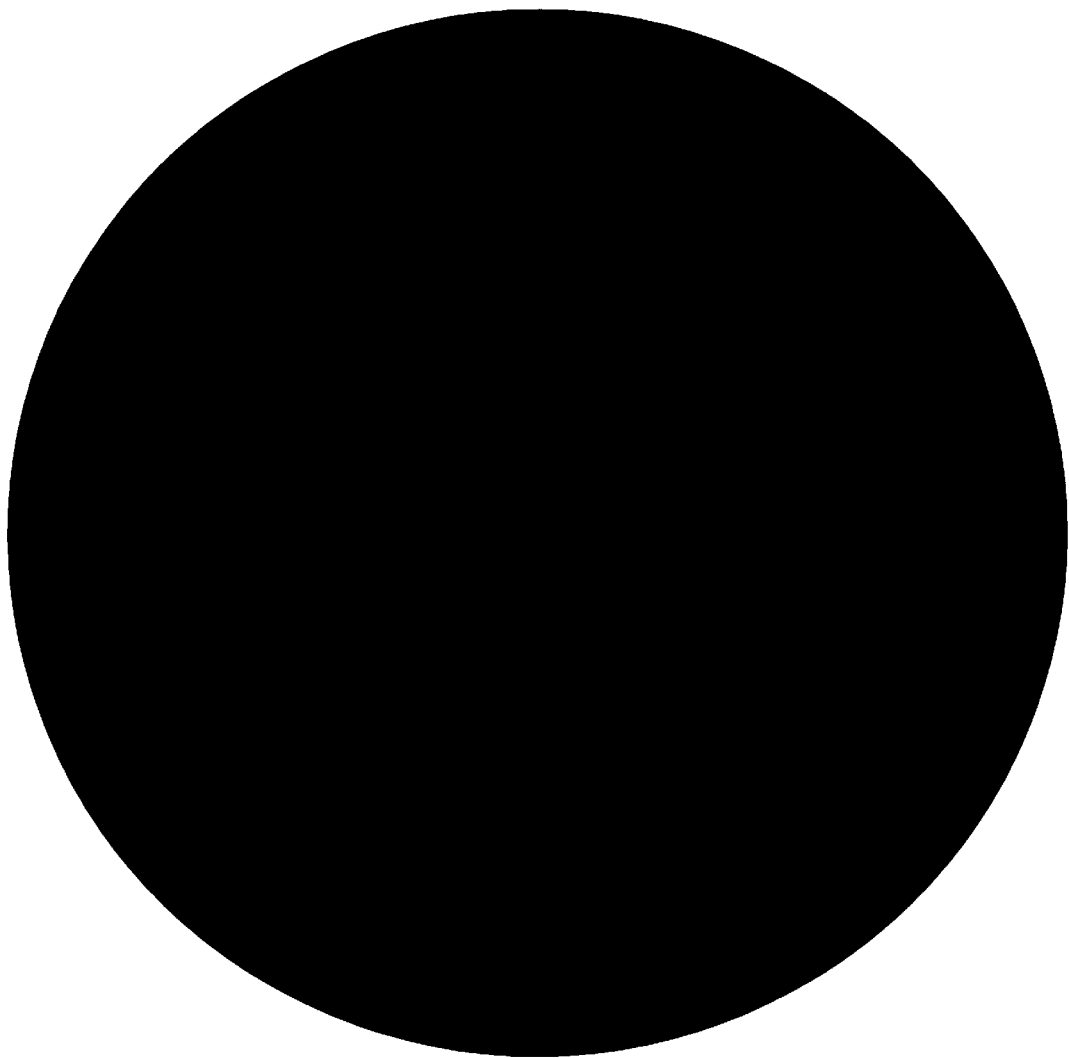
FIG. 15 is a front elevational view of a viewing target according to one embodiment of the present invention.

Horizontal calibrated scales 17 are disposed on body 2 via being affixed on or engraved into body 2 above upper horizontal slide slots 10a. Preferably, scales 17 are calibrated in millimeter increments and are situated approximately 45 mm from centerline A. Preferably, scales 17 have graduations from 20 mm to 40 mm. To determine horizontal pupil distance, an individual places the fitting frame on his or her head like he or she would place a pair of eyeglasses (as shown in FIG. 13). The individual then looks through pin holes 22 at an object preferably at least 20 feet away, e.g., the target shown in FIG. 15. The horizontal slides 11 and 12 are adjusted to provide an unobstructed view of the target. When the horizontal slides 11 and 12 are properly adjusted, measurements are taken by reading the graduation in alignment with lateral edges 15a and 15b.

Horizontal slides 11 and 12 have portions defining horizontal slide openings 18. Openings 18 are preferably 20 mm in length, 6 mm in width and are positioned approximately 8 mm from upper edges 11a and 12a of slides 11 and 12, respectively, and approximately 8 mm from lower edges 11b and 12b of slides 11 and 12, respectively. Vertical calibrated scales 19 are adjacent to, and laterally opposed to, relative to centerline A, openings 18. Preferably, scales 19 are 20 mm in height with millimeter graduations from −10 mm to 10 mm and are coextensive with openings 18.

In a preferred embodiment, horizontal slides 11 and 12 are 45 mm in width and 36 mm in height. Elongated tabs 14 are preferably 42 mm in length and 11 mm in height. An upper edge 14a of elongated tabs 14 preferably are situated 12.5 mm below upper edges 11a and 12a of horizontal slides 11 and 12. Tabs 13 are preferably 8 mm in width, 6 mm in height and approximately 17 mm from lateral edges 15a and 15b. In a preferred embodiment, an inner edge 13a of tabs 13 are centered over openings 18.

Situated on horizontal slides 11 and 12 are upper vertical slide slots 20a and lower vertical slide slots 20b adapted to slidingly engage vertical slides 21. Preferably, slots 20a and 20b are 12 mm in length. Slots 20a and 20b are adapted to receive vertical slides 21. Referring to FIGS. 1, 4, 5, and 6, vertical slides 21 have apertures 22 situated in the center of vertical slides 21. Preferably, apertures 22 are small in size like pin holes and are 1 mm in diameter but can range in diameter from about 0.5 mm to 1.5 mm. However, apertures 22 can conform to any regular or irregular geometric shape, e.g., a slot, a cross, an asterisk, an equilateral triangle, etc., so long as the individual using the fitting frame can focus on a distant object without obstruction when the fitting frame is properly adjusted to enable the individual to ascertain the individual's horizontal and vertical pupil distance.

Vertical slides 21 are preferably 80 mm in height and 11 mm in width. Vertical slides 21 are preferably sufficiently long to extend beyond upper edge 4a and lower edge 4 of body 2 to allow an individual to grasp ends 21a of vertical slides 21 and move the slides which are slidably engaged with horizontal slides 11 and 12 via slots 20 and 20b.

Preferably, a horizontal line 23 is disposed on vertical slides 21 via being affixed on or engraved in vertical slides 21 on the horizontal plane occupied by the center of aperture 22. To measure vertical pupil position, the individual places the fitting frame on his or her head like he or she would place a pair of eyeglasses (as shown in FIG. 13). The individual then looks through apertures 22 at an object preferably at least 20 feet away, e.g., the target shown in FIG. 15. The vertical slides 21 are adjusted to provide an unobstructed view of the target. When the vertical slides 21 are properly adjusted, measurements are taken by reading the graduation of scales 19 that are in alignment with line 23.

Referring to FIGS. 1, 2, 3, 7 and 8, temple members 7 and 8 have paired vertical temple slots 24 adapted to receive left temple slide 25 and right temple slide 26. Preferably slots 24 are 12 mm in height with the members of each pair being 6 mm apart and centered vertically within lateral ends 27 of temple members 7 and 8. Preferably, the innermost or medial slot of each pair is approximately 122 mm from the centerline A.

Temple slides 25 and 26 have, at distal ends, ear extensions 28 which are adapted to drape over an individual's ear at the uppermost point where the ear lobe meets the temporal region of the head. Ear extensions 28 are preferably continuous segments of temple slides 25 and 26 and are oriented at acute angles relative to a midline of temple slides 25 and 26 at junctures B which are formed by the junction of temple slides 25 and 26 and ear extensions 28. Preferably the acute angles formed by the temple slides 11 and 12 and ear extensions 28 are 45°.

Situated at inner or proximal ends of temple slides 11 and 12 are vertical sections 29. Vertical sections 29 are sized to act as an end stop to arrest horizontal movement of temple slides 11 and 12 laterally beyond slots 24. Calibrated temple scales 30 are disposed on temple members 7 and 8 via being affixed to, or engraved on, temple members 7 and 8 and preferably have graduations in millimeter increments from 20 mm to 50 mm. Preferably, the 20 mm graduation is aligned with score line 9. A measurement of the individual's temple length is taken by placing fitting frame 1 around the individual's head (as shown in FIG. 13), adjusting temple slides 11 and 12 to comfortably fit over the individual's ears and identifying the graduations of scales 30 that are in alignment with inner edges 31 of vertical sections 29.

In a preferred embodiment, temple slides 11 and 12 are 11 mm in width and 75 mm in length. Ear extensions 28 are preferably 11 mm in width and 48 mm in length. Vertical sections 29 are preferably 8 mm in width and 20 mm in height with the vertical centerline of the vertical sections 29 occupying the same plane as the longitudinal centerlines for temple slides 11 and 12.

Figure 9:
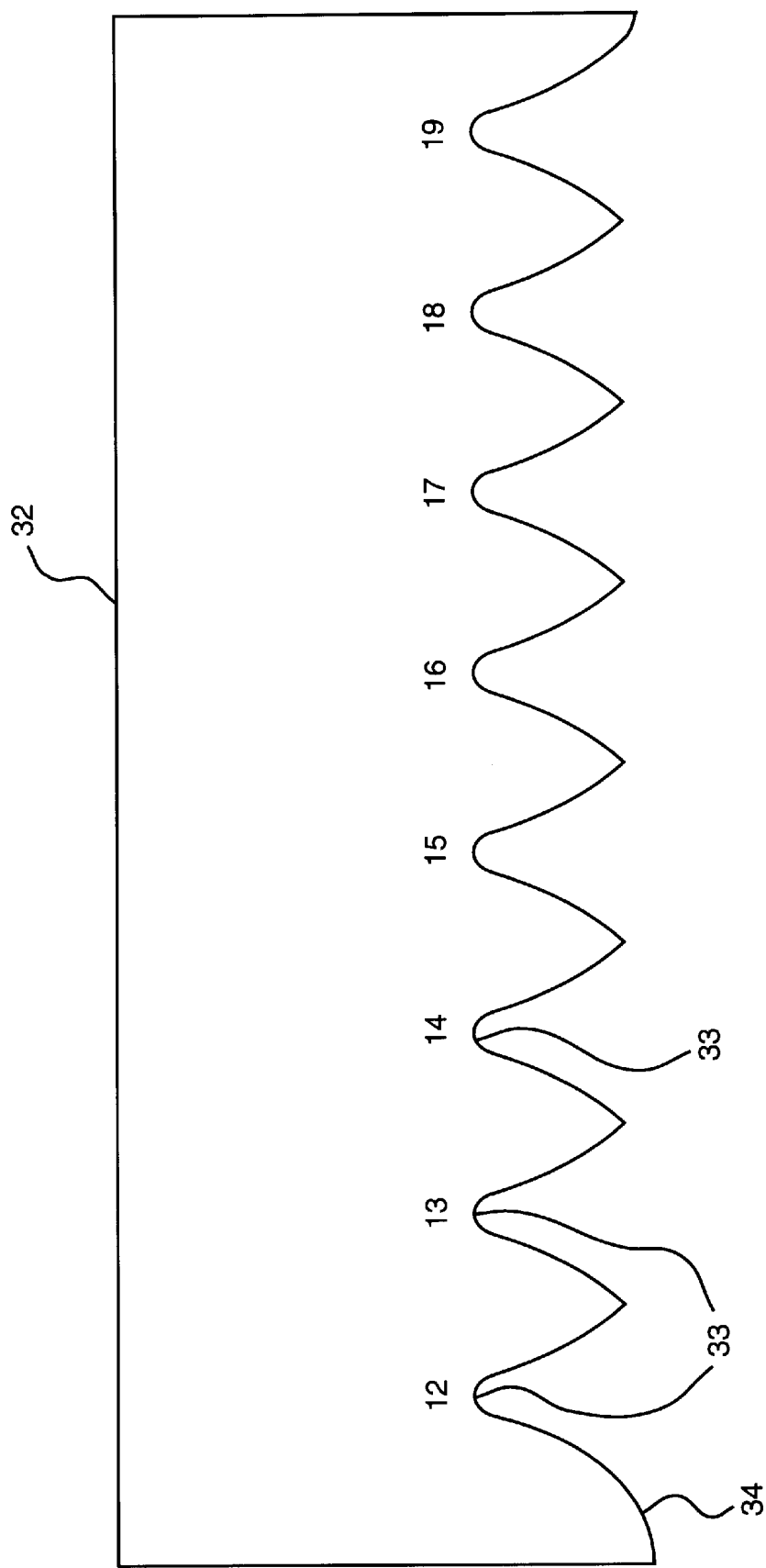
FIG. 9 is a front elevational view of a nose bar according to one embodiment of the present invention.

Referring to FIG. 9, a nose bar 32 of the fitting system is shown with incrementally-sized, parabolic-shaped curvatures 33 extending inwardly from a lower edge 34 of nose bar 32. To take a measurement of the individual's nose size, the individual places the nose bar across the bridge of the individual's nose using the various curvatures until a curvature is identified as fitting the most snug.

Figure 10:
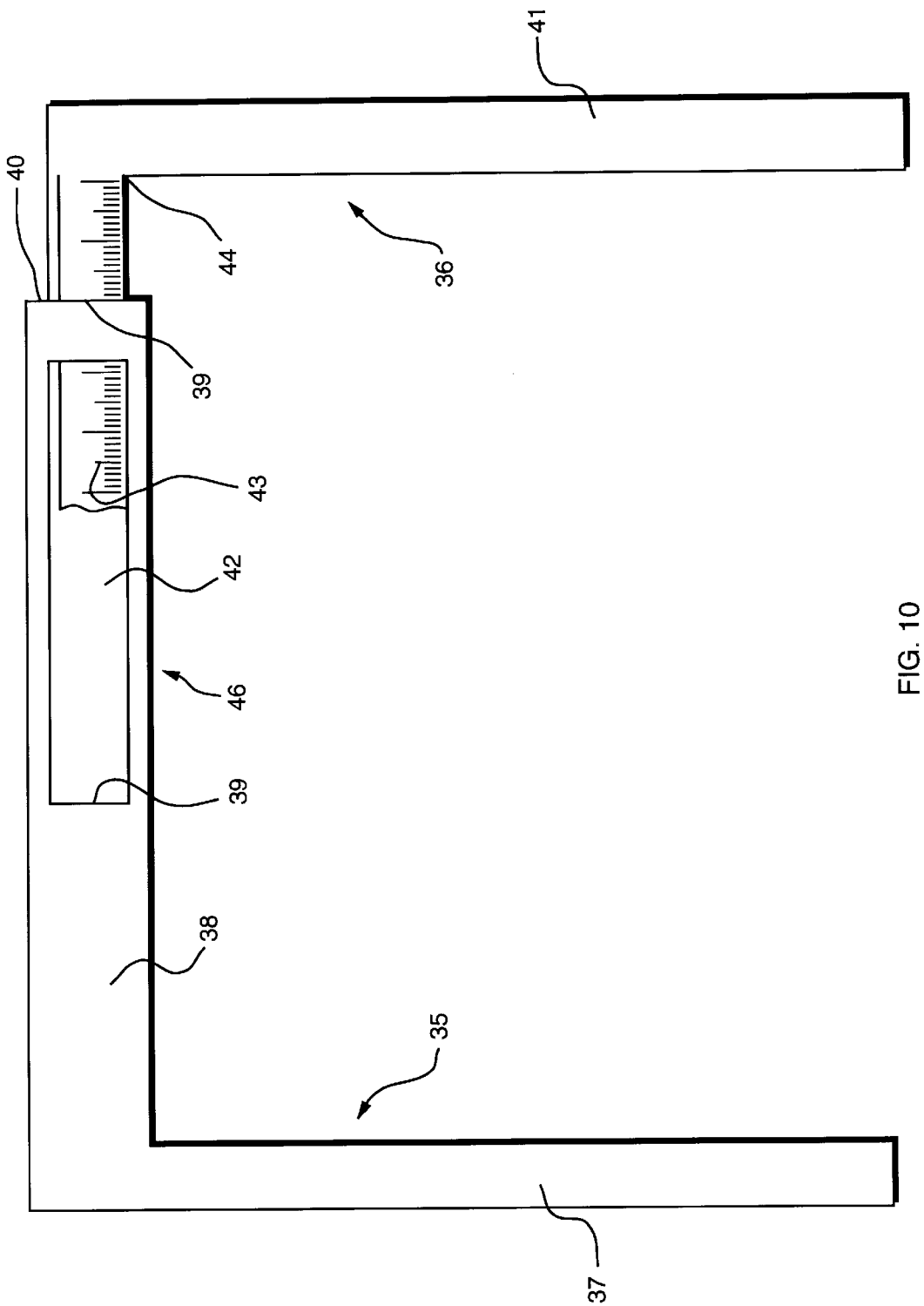
FIG. 10 is a top view of a head width slide according to one embodiment of the present invention.
Figure 12:
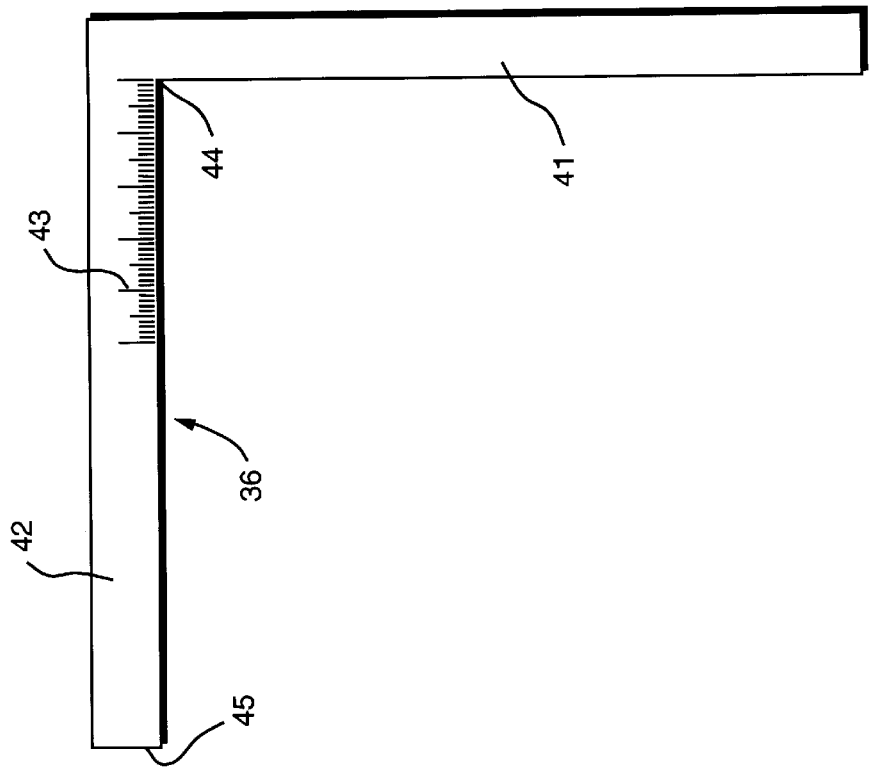
FIG. 12 is a top view of a right member of a head width slide according to one embodiment of the present invention.
Figure 11:
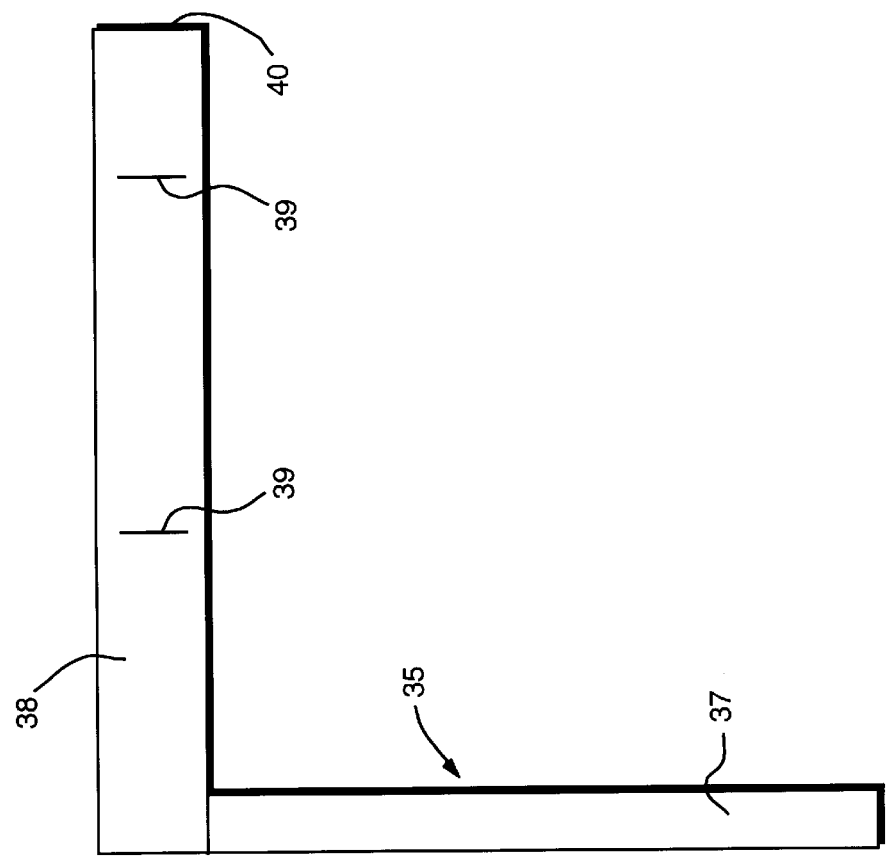
FIG. 11 is a top view of a left member of a head width slide according to one embodiment of the present invention.

Referring now to FIGS. 10, 11 and 12, a head width slide of the fitting system is depicted which is used to measure the overall width of the individual's head. The head width slide 46 is comprised of two L-shaped slidingly engageable segments, a first segment 35 and second segment 36. Segment 35 has a first temple leg 37 that is smaller in width than the width of a first segment forehead leg 38. Situated on forehead leg 38 are head width slide slots 39. In a preferred embodiment, slots 39 are 13 mm in height and are spaced apart approximately 72 mm. The slot 39 closest to a forehead leg edge 40 is spaced approximately 8 mm from leg edge 40. Preferably, temple leg 37 is 12 mm in width and 140 mm in length taken from an outside edge. Forehead leg 38 is preferably 20 mm in width and 142 mm in length taken from an outside edge.

A second segment 36 has a second segment temple leg 41 and a second segment forehead leg 42. Preferably, temple leg 41 is 12 mm in width and 136 mm in length taken from an outside edge. Forehead leg 42 is preferably 12 mm in width and 152 mm in length taken from an outside edge. Disposed on second segment forehead leg 42 via being affixed to, or engraved on, forehead leg 42 is a head width calibrated scale 43 situated at corner 44 of segment 36. Preferably, scale 43 has millimeter graduations from 30 mm, beginning at corner 44, to 80 mm. An end 45 of forehead leg 42 is inserted into slots 39 which are adapted to receive forehead leg 42 which is in sliding engagement with forehead leg 38.

Figure 14:
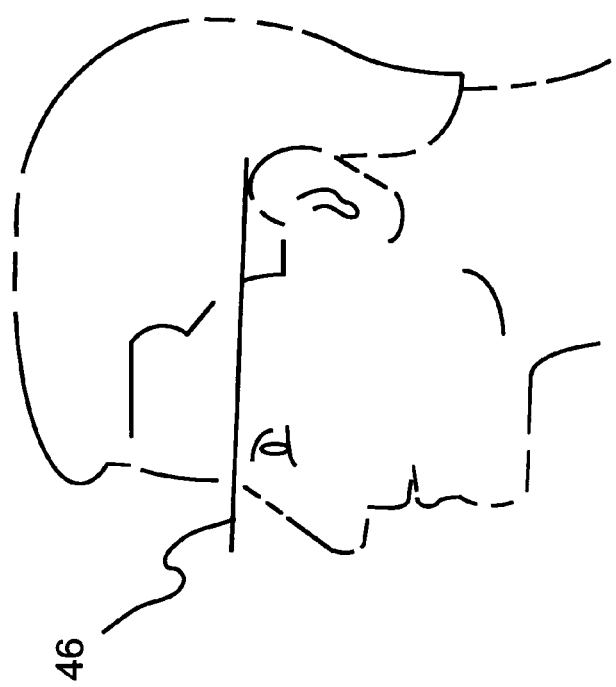
FIG. 14 is a side elevational view of an assembled fitting, according to one embodiment of the present invention, placed around an individual's head.

To measure head width, the individual places head width slide 46 around the individual's forehead with temple legs 37 and 41 resting on the individual's ear lobes at the point where the ear lobes meet the parietal region of the individual's head (as shown in FIG. 14). A reading is then taken of the graduation which is in alignment with end 40 of segment 35.

The fitting system can be made of any material such as cardboard or plastic. In a preferred embodiment, the fitting system comprising: the fitting frame, nose bar and head width slide is made of a durable grade of cardboard to reduce the cost of production and render the system readily disposable.

It is to be understood that the present invention is by no means limited to the particular constructions herein disclosed and/or shown in the drawings, but also comprises any modifications or equivalents within the scope of the claims.

Having thus described my invention, what I claim as new and desire to secure by United States Letters Patent is:

1. An eyeglass frame fitting kit comprising:
   a fitting frame having a body;
   a plurality of adjustable sliding segments in sliding engagement with said body wherein at least one of said sliding segments has an aperture;
   a head width slide having segments in sliding engagement for measuring an individual's head width; and
   a nose bar having a plurality of curvatures for measuring the individual's nose size.

2. The eyeglass frame fitting kit of claim 1 wherein the body has a parabolic-shaped curvature adapted to matingly engage the contour of the individual's nose.

3. The eyeglass frame fitting kit of claim 2 wherein the parabolic-shaped curvature is situated about a centerline of the body with ends terminating on a bottom edge of the body.

4. The eyeglass frame fitting kit of claim 3 wherein the parabolic-shaped curvature has sides which are about 8.5 millimeters from the centerline when measured from a point 10 millimeters below an apex of the parabolic-shaped curvature.

5. The eyeglass frame fitting kit of claim 1 wherein the body has portions defining two openings situated equidistant about a centerline of the body.

6. The eyeglass frame fitting kit of claim 1 wherein the fitting frame further comprises a left temple member and a right temple member situated on opposite sides of the body such that each temple member is in mechanical connection with the body and rotatable about an axis of connection.

7. The eyeglass frame fitting kit of claim 6 wherein a vertical score line is provided at a junction of the body and temple members such that the temple members can rotate about the score line in relation to the body.

8. The eyeglass frame fitting kit of claim 6 wherein the left and right temple members each have paired temple slots adapted to receive a left and a right temple slide which comprise two of the plurality of adjustable sliding segments.

9. The eyeglass frame fitting kit of claim 8 wherein the temple slides have, at distal ends, ear extensions adapted to drape over an individual's ear.

10. The eyeglass frame fitting kit of claim 8 wherein the temple slides have vertical sections at medial ends of the temple slides that are sized and adapted to arrest horizontal movement of the temple slides laterally beyond the temple slots.

11. The eyeglass frame fitting kit of claim 10 wherein the temple members have graduated scales disposed thereon and situated to align with inner edges of the temple slide vertical sections.

12. The eyeglass frame fitting kit of claim 1 wherein two of the adjustable sliding segments are a left horizontal slide and a right horizontal slide.

13. The eyeglass frame fitting kit of claim 12 wherein the horizontal slides have tabs adapted to slidingly engage the body via slots situated on the body.

14. The eyeglass frame fitting kit of claim 13 wherein the slots comprise two upper horizontal slide slots and two lower horizontal slide slots.

15. The eyeglass frame fitting kit of claim 14 wherein the upper horizontal slide slots are situated above portions of the body defining two openings situated equidistant about a centerline of the body; and,
   the lower horizontal slide slots are situated below the two openings.

16. The eyeglass frame fitting kit of claim 15 wherein horizontal calibrated scales are disposed on the body above the upper horizontal slide slots.

17. The eyeglass frame fitting kit of claim 14 wherein the left and right horizontal slides have elongated tabs extending laterally therefrom with each elongated tab extending beyond one of the opposite ends of the body, wherein each elongated tab is adapted to slidingly engage the body via paired elongated tab slots in the body.

18. The eyeglass frame fitting kit of claim 14 wherein the horizontal slides have portions defining horizontal slide openings.

19. The eyeglass frame fitting kit of claim 18 wherein vertical calibrated scales are disposed on the horizontal slides adjacent to, and laterally opposed to, relative to a centerline of the body, the horizontal slide openings.

20. The eyeglass frame fitting kit of claim 19 wherein the vertical calibrated scales are coextensive with the horizontal slide openings.

21. The eyeglass frame fitting kit of claim 14 wherein the horizontal slides have disposed thereon upper and lower vertical slide slots.

22. The eyeglass frame fitting kit of claim 21 wherein the vertical slide slots are adapted to slidingly engage vertical slides which comprise two of the plurality of adjustable sliding segments.

23. The eyeglass frame fitting kit of claim 22 wherein the vertical slides have apertures situated therein.

24. The eyeglass frame fitting kit of claim 23 wherein the apertures are situated in the center of the vertical slides.

25. The eyeglass frame fitting kit of claim 23 wherein the apertures are pin holes which are about between 0.5 and 1.5 millimeters in diameter.

26. The eyeglass frame fitting kit of claim 25 wherein the apertures are pin holes which are 1 millimeter in diameter.

27. The eyeglass frame fitting kit of claim 23 wherein the apertures conform to regular or irregular geometric shapes.

28. The eyeglass frame fitting kit of claim 27 wherein the vertical slides have horizontal lines disposed thereon, wherein the horizontal lines are situated in a horizontal plane occupied by the center of the apertures.

29. The eyeglass frame fitting kit of claim 1 wherein the nose bar has parabolic-shaped curvatures.

30. The eyeglass frame fitting kit of claim 29 wherein the parabolic-shaped curvatures are incrementally sized and extend inwardly from a lower edge of the nose bar.

31. The eyeglass frame fitting kit of claim 1 wherein the head width slide is comprised of two L-shaped slidingly engageable segments, a first L-shaped segment and a second L-shaped segment.

32. The eyeglass frame fitting kit of claim 31 wherein a first L-shaped segment has a first segment temple leg and a first segment forehead leg.

33. The eyeglass frame fitting kit of claim 32 wherein the first segment forehead leg has head width slide slots adapted to slidingly engage a second L-shaped segment which has a second segment temple leg and a second segment forehead leg.

34. The eyeglass frame fitting kit of claim 33 wherein the second segment forehead leg has a head width calibrated scale disposed thereon.

35. The eyeglass frame fitting kit of claim 34 wherein the second segment forehead leg is sized to be inserted into the head width slide slots of the first L-shaped segment.

36. An eyeglass frame fitting kit comprising:
a fitting frame having a body with portions defining two openings situated about a centerline of the body, and a parabolic-shaped curvature adapted to engage the contour of an individual's nose;
temple members situated on opposite sides of the body and in mechanical connection with the body, wherein the temple members are rotatable about an axis of connection;
two horizontal slides having portions defining horizontal slide openings, tabs adapted to slidingly engage the body via horizontal slide slots situated on the body and, elongated tabs extending laterally from the horizontal slides such that the elongated tabs extend beyond the sides of the body;
vertical calibrated scales disposed on the horizontal slides for measuring vertical pupil distance;
horizontal calibrated scales disposed on the body adjacent to the horizontal slides for measuring horizontal pupil distance;
vertical slides in sliding engagement with the horizontal slides via vertical slide slots adapted to receive the vertical slides and sized to extend beyond a bottom and a top edge of the body;
apertures and horizontal lines situated in the vertical slides wherein the apertures and horizontal lines occupy the same plane;
temple slides having ear extensions at a distal end and vertical sections at a proximal end in sliding engagement with the temple members via temple slots disposed in the temple members wherein the vertical sections are sized and adapted to arrest horizontal movement of the temple slides laterally beyond the temple slots;
graduated scales disposed on the temple members to measure temple length;
a nose bar having incrementally-sized parabolic-shaped curvatures extending inwardly from a lower edge of the nose bar;
a head width slide having two L-shaped segments wherein a first L-shaped segment has a first segment temple leg and a first segment forehead leg and a second L-shaped segment has a second segment temple leg and a second segment forehead leg, wherein the second segment is slidingly engageable with the first segment via head width slide slots on the first segment; and
a head width calibrated scale disposed on the second L-shaped segment to measure head width.

37. The eyeglass frame fitting kit of claim 36 wherein the apertures are pin holes with a dimension of about between 0.5 and 1.5 millimeters.

38. The eyeglass frame fitting kit of claim 36 wherein the apertures are pin holes with a dimension of about 1 millimeter.

39. A method of taking measurements to fit eyeglasses to an individual comprising:
providing a fitting frame having a body and a plurality of adjustable sliding segments in sliding engagement with said body and wherein at least one of said sliding segments has an aperture;
placing said fitting frame on the individual to take measurements of horizontal pupil distance, vertical pupil distance and temple length;
providing a head width slide having two segments in sliding engagement;
placing said head width slide on the individual to take a head width measurement;
providing a nose bar with a plurality of curvatures; and,
placing said nose bar on the individual's nose to take a nose size measurement.

40. The method of claim 39 further comprising the steps of
sighting a distant object through the apertures; and adjusting the adjustable slide segments to provide an unobstructed view of the distant object.

41. The method of claim 40 further comprising the steps of:

adjusting horizontal slides in sliding engagement with the fitting frame body to provide an unobstructed view of the distant object and, determining horizontal pupil distance by reading graduations on horizontal calibrated scales, disposed on the fitting frame body that are in alignment with lateral edges of the horizontal slides.

42. The method of claim 41 further comprising the steps of:

adjusting vertical slides in sliding engagement with the horizontal slides to provide an unobstructed view of the distant object and, determining vertical pupil distance by reading graduations on vertical calibrated scales, disposed on the horizontal slides that are in alignment with horizontal lines disposed on the vertical slides on horizontal planes occupied by a center of the apertures.

43. The method of claim 42 further comprising the steps of:

providing temple slides having vertical sections on a proximal end and ear extensions at a distal end, the temple slides being in sliding engagement with temple members via temple slots disposed on the temple members;

adjusting the temple slides to fit over the individual's ear; and, determining temple length by reading graduations on calibrated temple scales disposed on the temple members that are in alignment with inner edges of the vertical sections.

44. The method of claim 43 further comprising the steps of:

providing a head width slide with segments having temple legs;

placing the head width slide around the individual's head with the temple legs resting on the individual's ear lobes; and, determining the individual's head width by reading graduations on a head width calibrated scale disposed on a first segment of the head width slide that is in alignment with an end of a second segment.

45. An eyeglass fitting frame for determining horizontal and vertical pupil distance comprising:

a body; and a plurality of adjustable sliding segments in sliding engagement with said body wherein at least one of said sliding segments has an aperture configured to measure horizontal and vertical pupil distance.

46. The eyeglass fitting frame of claim 45 wherein the body has a parabolic-shaped curvature adapted to matingly engage the contour of the individual's nose, wherein the parabolic-shaped curvature is situated about a centerline of the body with ends terminating on a bottom edge of the body.

47. The eyeglass fitting frame of claim 45 wherein the fitting frame further comprises a left temple member and a right temple member situated on opposite sides of the body such that each temple member is in mechanical connection with the body and rotatable about an axis of connection.

48. The eyeglass fitting frame of claim 47 wherein the left and right temple members each have paired temple slots adapted to receive a left and a right temple slide which comprise two of the plurality of adjustable sliding segments.

49. The eyeglass fitting frame of claim 48 wherein the temple slides have, at distal ends, ear extensions adapted to drape over an individual's ear.

50. The eyeglass fitting frame of claim 49 wherein the temple slides have vertical sections at proximal ends of the temple slides that are sized and adapted to arrest horizontal movement of the temple slides laterally beyond the temple slots.

51. The eyeglass fitting frame of claim 45 wherein two of the adjustable sliding segments are a left horizontal slide and a right horizontal slide, wherein the horizontal slides have tabs adapted to slidingly engage the body via slots situated on the body.

52. The eyeglass fitting frame of claim 51 wherein the horizontal slides have disposed thereon upper and lower vertical slide slots adapted to slidingly engage vertical slides which comprise two of the plurality of adjustable sliding segments.

53. The eyeglass fitting frame of claim 51 wherein the vertical slides have apertures situated therein.

54. The eyeglass fitting frame of claim 53 wherein the apertures are pin holes which are about between 0.5 and 1.5 millimeters in diameter.

55. The eyeglass fitting frame of claim 53 wherein the apertures are pin holes which are 1 millimeter in diameter.

56. The eyeglass fitting frame of claim 53 wherein the apertures conform to regular or irregular geometric shapes.

* * * * *